(12) United States Patent
Hartenstein et al.

(10) Patent No.: US 6,476,915 B2
(45) Date of Patent: Nov. 5, 2002

(54) METHOD OF MEASURING THE QUALITY PROPERTIES OF PAPER AND/OR BOARD ON MOVING WEBS

(75) Inventors: Hermann Hartenstein, Neunkirchen; Uwe Lampe, Buxtehude, both of (DE); Christoph Roth, Tokyo (JP)

(73) Assignee: Siemens Aktiengesellschaft AG, Munich (DE)

(*) Notice: Subject to any disclaimer, the term of this patent is extended or adjusted under 35 U.S.C. 154(b) by 0 days.

(21) Appl. No.: 09/849,016

(22) Filed: May 4, 2001

(65) Prior Publication Data

US 2001/0028459 A1 Oct. 11, 2001

Related U.S. Application Data

(63) Continuation of application No. PCT/DE99/03510, filed on Nov. 3, 1999.

(30) Foreign Application Priority Data

Nov. 4, 1998 (DE) .......................... 198 50 825

(51) Int. Cl.[7] .................. G01N 21/84; G01N 37/00; G06F 19/00; G06G 7/48
(52) U.S. Cl. .................. 356/429; 700/122; 703/12; 702/84
(58) Field of Search ................ 356/429, 407, 356/408, 425, 430; 250/226, 559.04; 703/4, 12; 702/182, 108, 81–84; 700/95, 97, 109, 110, 117, 127, 122, 128, 129

(56) References Cited

U.S. PATENT DOCUMENTS

| | | | | |
|---|---|---|---|---|
| 5,680,321 A | * | 10/1997 | Helmer et al. | 364/499 |
| 5,842,150 A | * | 11/1998 | Renberg et al. | 702/23 |
| 6,111,651 A | * | 8/2000 | Shakespeare | 356/429 |
| 6,272,440 B1 | * | 8/2001 | Shakespeare et al. | 702/85 |

FOREIGN PATENT DOCUMENTS

| | | |
|---|---|---|
| DE | 19653532 | 6/1998 |
| DE | 19830323 | 1/1999 |
| DE | 19827525 | 12/1999 |
| EP | 0745917 | 12/1996 |
| WO | 9531713 | 11/1995 |
| WO | 9738305 | 10/1997 |
| WO | 9828488 | 7/1998 |

* cited by examiner

Primary Examiner—Michael Stafira
(74) Attorney, Agent, or Firm—BakerBotts LLP

(57) ABSTRACT

A method for measuring the quality properties of paper and/or board on moving webs is disclosed. The present invention utilizes a staged evaluation method in which the basic properties of the paper or board and further properties are determined via multi-stage modeling.

21 Claims, 5 Drawing Sheets

METHOD OF MEASURING THE QUALITY PROPERTIES OF PAPER AND/OR BOARD ON MOVING WEBS

SPECIFICATION

This application is a continuation of PCT/DE99/03510, filed Nov. 3, 1999.

FIELD OF THE INVENTION

The present invention generally relates to a method of measuring the quality properties of paper and/or board on moving webs. In particular, the present invention relates to using optical contactless methods in a continuous optical spectra, preferably in the infra-red range, for measuring and evaluating the quality properties of paper and/or board on moving webs by chemometric methods.

BACKGROUND OF THE INVENTION

In DE 198 30 323 A1, a method and an associated apparatus for determining the thickness of paper or board on a moving web are described in which measurements are made optically without contact and the spectra are evaluated by chemometric methods. DE 198 30 343 A1 discloses a thickness measuring method and associated apparatus which use chemometric evaluation of the optical spectral lines obtained on one side of the web from a light source on the opposite side of the web. The thickness of the web is determined by comparing training sets for a number of different material characteristics. The spectral lines can be detected via an on-line spectrometer with at least one light source on one side of the web and a number of detectors on the opposite side for detecting the transmitted light components, e.g. in the infra-red range.

SUMMARY OF THE INVENTION

The present invention provides a method for registering the properties of paper or board. The present invention utilizes a staged evaluation method. In the staged evaluation method, first, the basic properties of the paper or the board are determined and then further properties are determined via multi-stage modeling. In an exemplary embodiment, the basic properties determined are preferably: the grammage, the moisture and/or the thickness (caliper) of the paper or board. It is also preferable to perform three-stage modeling where the material composition, freeness and further individual variables are determined one after another.

Using the multi-stage modeling, the present invention determines and evaluates all variables measured for the interested quality properties of the paper or board without traversing, by means of suitable on-line modeling, unlike that disclosed in DE 198 30 323 A1 which only determined paper thickness.

BRIEF DESCRIPTION OF THE DRAWINGS

For a complete understanding of the present invention and the advantages thereof, reference is now made to the following description taken in conjunction with the accompanying drawings in which like reference numbers indicate like features, components and method steps, and wherein.

DETAILED DESCRIPTION OF THE INVENTION

Infrared spectroscopy in the NIR range (near infra-red) and the MIR range (medium infra-red) is a known method for the identification of chemical compounds qualitatively using their specific absorption, and of making quantitative statements on the basis of the absorption intensity. In specific terms, paper is a mixture of materials from organic raw materials, such as bleached and unbleached chemical pulps and mechanical pulps, inorganic constituents, such as fillers and the coating (as it is known) on the finished paper, and also from other organic auxiliary materials, such as sizing agents, wet-strengthening agents and the like. It has been shown that it is possible, with the aid of IR (infra-red) spectroscopy in the NIR range or the MIR range, to identify the aforementioned constituents and to determine them quantitatively by registering and evaluating continuous spectra.

Figure 1:
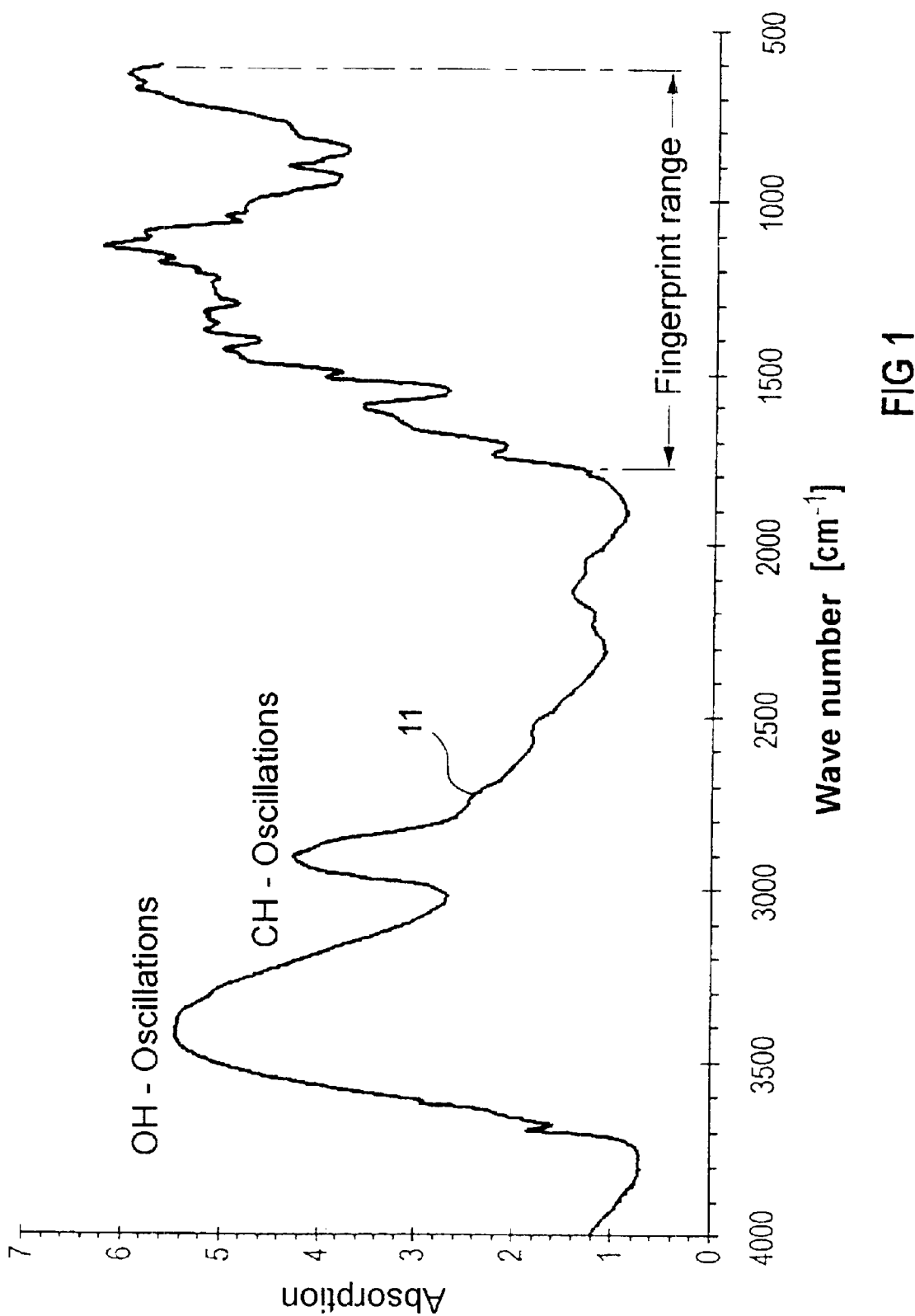
FIG. 1 is a graph which illustrates a continuous spectrum for paper.

Now referring to the drawings, FIG. 1 illustrates a spectrum 11 for paper for which the quality properties need to be determined and evaluated. In FIG. 1, the absorption is plotted against the wave number. The important factor for the further evaluation is the spectral range at wave numbers between about 3500 $cm^{-1}$ and about 3000 $cm^{-1}$, in which significant structures result from the action of the OH oscillations and CH oscillations, and also the range above 1800 $cm^{-1}$, which is referred to as the fingerprint range and permits statements to be made about quality properties of paper, in particular.

Relevant quality properties of paper, which are substantially also determined by the thickness of the paper are, for example, the freeness, the air penetration resistance and the mechanical strengths and the optical properties.

With regard to the freeness, it is assumed that as a result of the refining, the chemical pulp and mechanical fibers as the raw material for the paper are changed mechanically, in particular, they are shortened or defibrillated. The change in the particle size has a direct effect on the optical properties, such as the light scattering, which is reflected in the spectrum. In addition, changes in the chemical structure of the fibers can also be detected. In particular, the proportion of hemicellulosis at the fiber surface, and the strength and the density of the intermolecular and intramolecular hydrogen-bridge bonds in the cellulose are changed by the refining.

Figure 3:
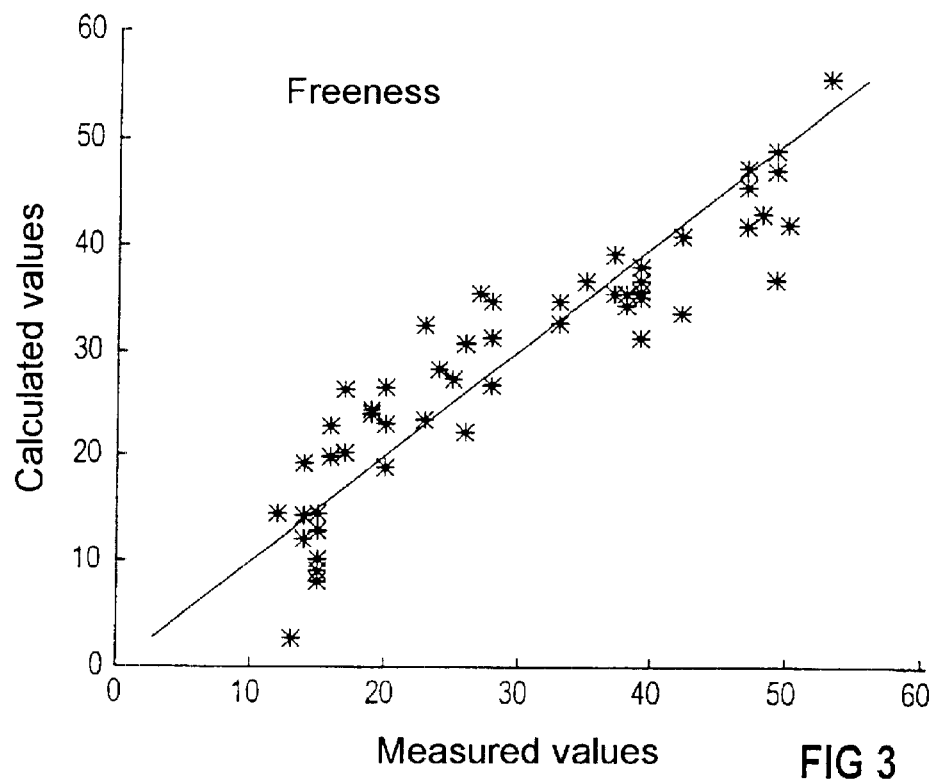
FIG. 3 is a graph which illustrates a comparison of measured and calculated values for the freeness.
Figure 4:
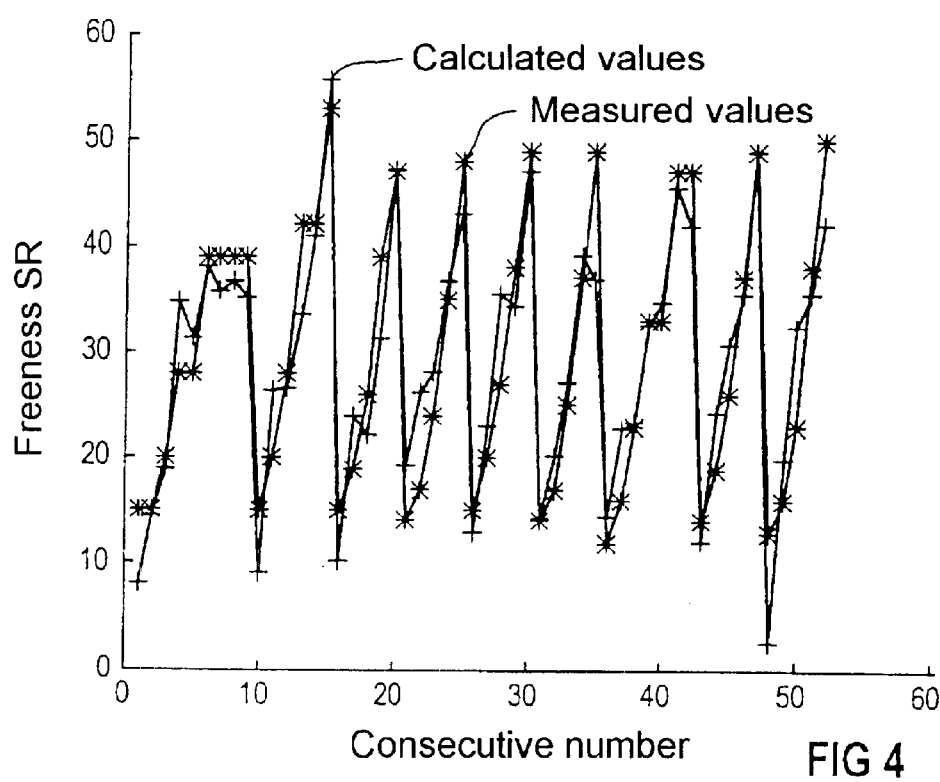
FIG. 4 is a graph which illustrates the freeness over a collection of samples.

Such changes in the chemical structure are visible in the infrared spectrum. In particular, a correlation can be determined between the changes observed in the spectrum and the freeness, which is illustrated in FIGS. 3 and 4. FIG. 3 illustrates the calculated values of the freeness SR as a function of the measured values, the result showing a sufficiently good correlation. FIG. 4 illustrates the freeness using a collection of samples, with measured and calculated values. In FIGS. 3 and 4, the results include the modeling of the freeness on the basis of the infra-red spectra for paper made of bleached coniferous and sulfate pulp.

The air penetration resistance (the porosity of the paper), is substantially influenced by the fiber size and the density of the fiber packing. Investigations confirm that there is a correlation with the structures of infra-red spectra.

Finally, the mechanical strengths of the paper correlate, in a similar way to the freeness, to the fiber size, fiber shape and the fiber strengths, in particular, the bonding strength of the fibers, the bonding strengths between the fibers and the fiber orientation, which is also referred to as formation. The bonding strength within and between the fibers is primarily determined by the strengths and density of the hydrogen bridges between the cellulose molecules. WO 97/38305 A1 confirms that the presence of hydroxyl and/or carboxyl groups bounding to one another at the fiber surface is registered optically.

The aforementioned factors have an influence on the spectra of papers in the NIR (near infra-red) or MIR (medium infra-red) range, so that it may be assumed that there is a correlation between the spectra and the mechanical strengths. These assumptions are confirmed in the graph of FIG. 5, which illustrates the correlation between the modeling of the CMT (chemical mechanical temperature) values and measured properties.

Figure 6:
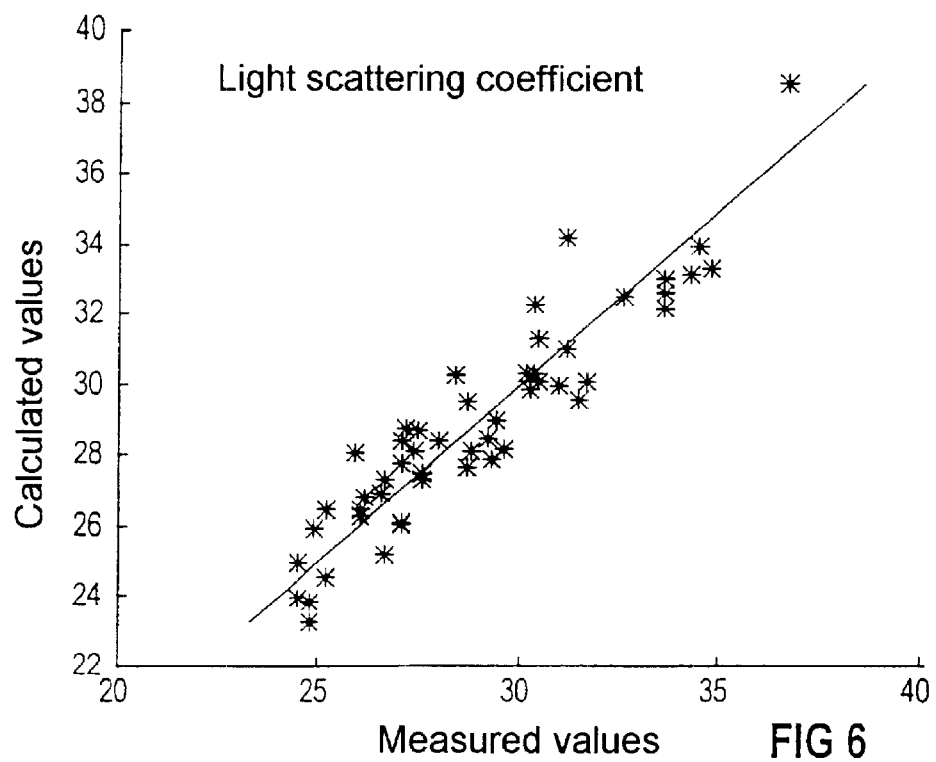
FIG. 6 is a graph illustrating the comparison of calculated and measured values for the light scattering coefficient.
Figure 7:
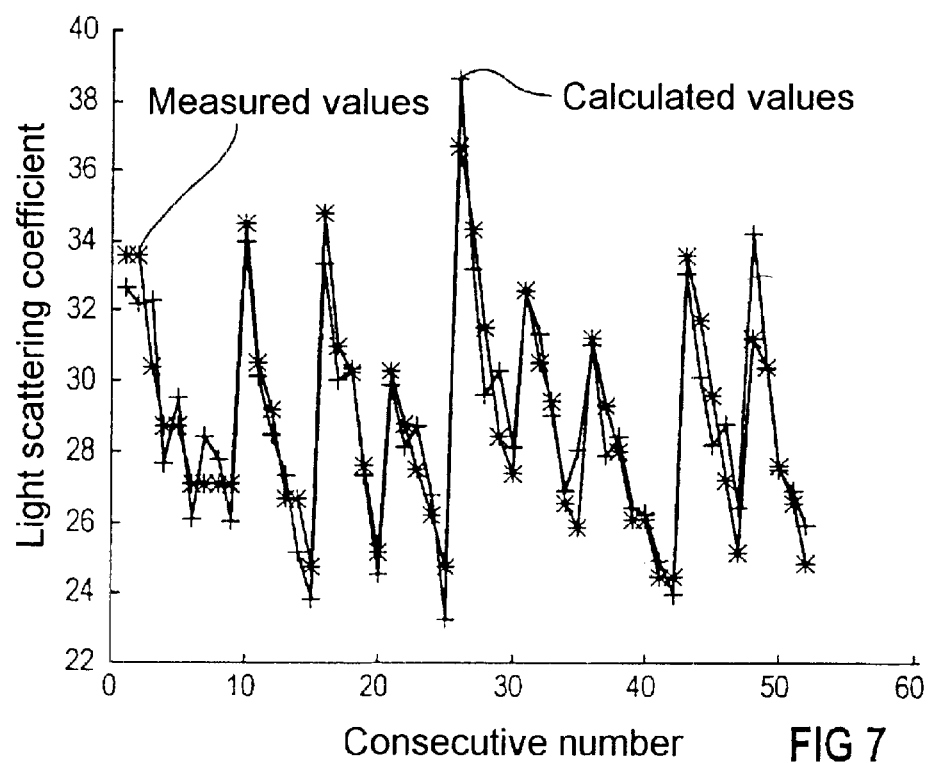
FIG. 7 is a graph which illustrates the light scattering coefficient over a collection of measured samples.

Finally, the optical properties, which can be determined directly by means of measurement with visible light, are also of importance. These are light scattering effects, which can also be determined by means of measurement with the IR spectra, and also material properties, which can be determined directly by means of the material composition. FIGS. 6 and 7 illustrate the results of such modeling, specifically for the light scattering coefficients for paper made of bleached coniferous sulfate pulp (BSK).

The measurement of the spectra can be performed in a straightforward way, in particular with a sensor array corresponding to the earlier German Patent Application 198 30 323.8, the array being integrated in a measuring frame spanning the moving paper web. In order to increase the number of measurement points, a system can be provided with which the entire measuring frame is moved transversely with respect to the paper web, corresponding to the earlier German Patent Application 197 29 005. 1, the measurement being synchronized with the frame movement. As mentioned above, the measurement is carried out in the infra-red range, continuous spectra with wavelengths from 1 to 2.5 $\mu$m (NIR) and/or 2.5 to 20 $\mu$m (MIR) being registered. The measurement is carried out as a function of grammage, in transmission or diffusion or direct reflection.

The spectra obtained in this way are evaluated following mathematical preconditioning with the aid of chemometric methods, such as, in a preferred embodiment, the known methods of partial least square (PLS) or partial component analysis (PCA), and multivariable data analysis or the use of neural networks. The present invention's multi-stage method is used for analysis, as is illustrated in detail using FIG. 2.

Figure 2:
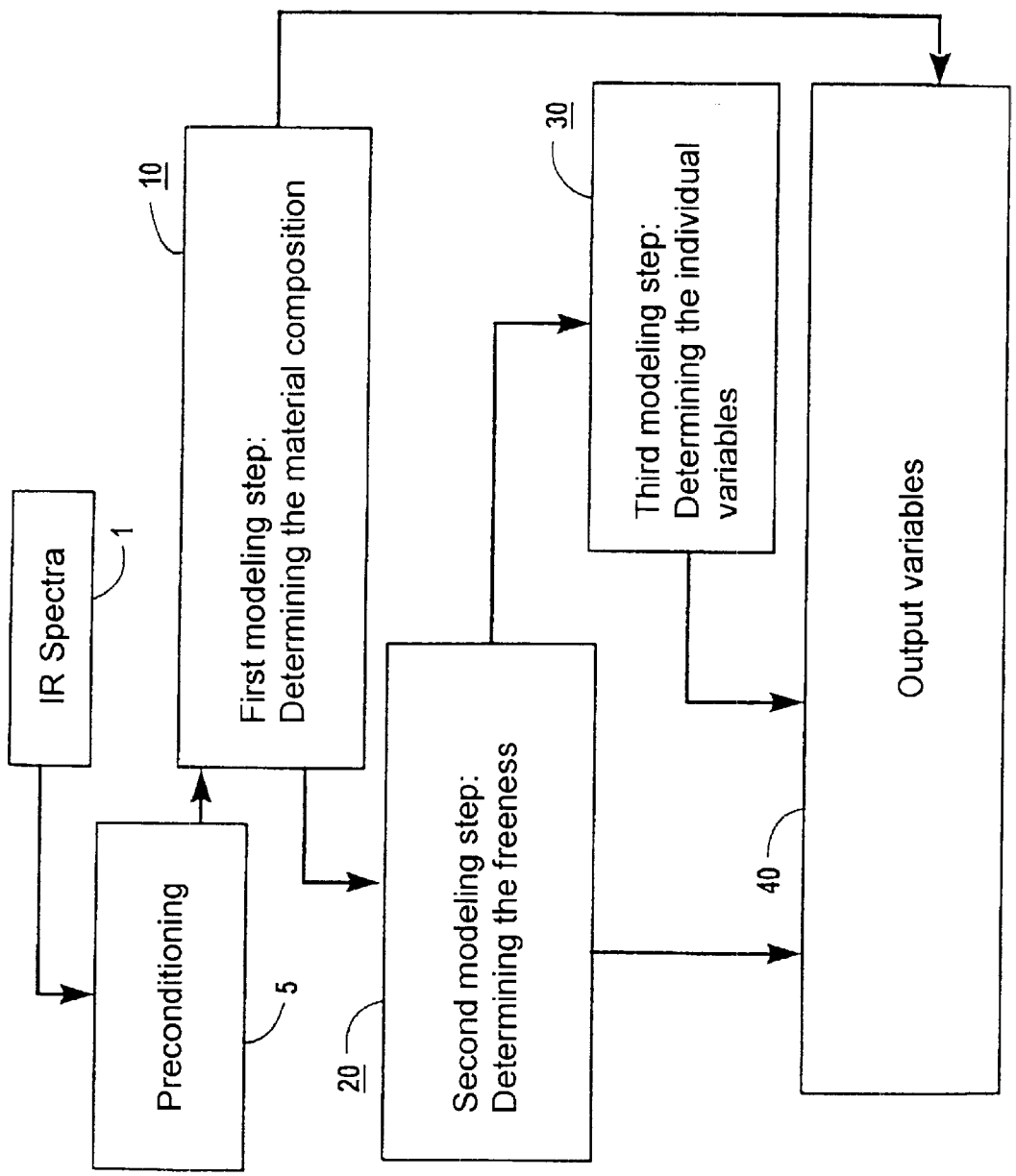
FIG. 2 is a flow chart illustrating the procedure during the evaluation with step-by-step modeling.

In FIG. 2, a registration block for the measured IR spectra is designated by 1. In a unit 5, preconditioning is performed followed by individual modeling units. In a first modeling unit 10, into which as input the preconditioned spectra are entered for further evaluation, the material composition is determined in a first step in the modeling. The output is, for example, the content of fibrous materials, of fillers and of auxiliary materials. In addition, the coating (as it is known) can be determined and output as a paper property.

In a second modeling unit 20, into which the results of the first modeling unit 10, which is the processed spectra and, in particular, the content of fibrous materials, are entered as input, in the second step further modeling determines the freeness from the content of fibrous materials. Specifically, the freeness is specified as a result from the second modeling unit 20 and evaluated further in a third modeling unit 30.

With the entry of the processed spectra, the content of fibrous materials, the freeness, the content of fillers and the further auxiliary materials, the individual variables are then evaluated in the unit 40. At the same time, the freeness is taken into account as a result of the second modeling step.

The model output which results from the unit 40 is in each case separate models for the basic variables, for the composition, for the mechanical strength and for the optical properties. The basic variables specified are the grammage, the moisture, the thickness and the ash content of the paper. The variables for the composition are the fillers, the coating and the auxiliary materials. The variables which result for the mechanical properties are the tearing strength, the bursting strength and the tear propagation work, as quality parameters which are significant in practice. The variables which result for the optical properties are the light absorption, opacity and the light scattering. Using all of the above variables, a paper and/or board can be described comprehensively in terms of its quality properties.

Referring to FIGS. 1 and 2, unit 1, for preconditioning the spectra, comprises the formation of averages, smoothing the spectra and the formation of derivatives. In the process, very distorted parts of the spectra can be eliminated for further processing. In the subsequent units 10, 20 and 30, dedicated models are set up for each of the variables to be determined, different spectral ranges and preconditioning also being expedient for calculating the individual measured variables in an individual case. As mentioned, chemometric methods, such as PCA and PLS, multivariable data analysis and/or neural networks are used for the modeling.

As mentioned above, the modeling is composed of three steps which are summarized again below with their characteristics. The first step in the modeling according to unit 10 comprises the determination of the qualitative and quantitative material composition of the paper. A classification follows in accordance with fibrous materials and the determination of their proportion, specifically:

BSK=bleached softwood Kraft

BHK=bleached hardwood Kraft

BHS=bleached hardwood sulfite

UBSK=unbleached softwood Kraft

TMP=thermomechanical pulp (refiner pulp)

CTMP=chemothermomechanical pulp (refiner pulp with chemical conversion)

GW=groundwood.

These variables can be used as a selection criterion for the model in the next calculation step, specifically the determination of the fillers and the coating (the coating on the paper as it is known). These are specifically:

calcium carbonate kaolin (china clay)

titanium dioxide barium sulfate.

The model variables may be a measured variable or a quality parameter to be determined and can be used for controlling the input of filler or the coating process, or can be used as an input parameter for the following models. In addition, a determination is made of the auxiliary materials, such as the sizing agent or wet-strength materials.

Using the models selected in the first modeling step, the freeness is determined. Depending on the material composition registered in the specific application, for example in the case of produced papers, it is necessary for a plurality of models to be set up for the calculation of the freeness. The output from this model may also be a measured variable to be determined and is used, for example, for control of the refiners used upstream of the paper machine. Using the material composition and the freeness determined in accordance the present invention, a suitable model is determined for calculating the further paper properties.

Depending on the material type according to unit 10 and the freeness according to unit 20, in the third step, in the unit 30, the basic properties of grammage, moisture, thickness, air penetration resistance, of the paper are determined with individual partial models. In addition, using suitable partial models, the mechanical strengths, such as, tearing length, bursting strength, tear propagation work, modulus of elasticity, extension at break, and also the optical properties, such as light scattering coefficient, light absorption coefficients, opacity, reflection factor, may be determined. The number of models to be used depends on the number of variables to be measured, the variety of substances and the freenesses.

The selection of the respective model which applies to the material composition and the freeness can be carried out automatically on the basis of the evaluation of the infra-red spectra. However, in order to assist this process, a set point may be provided from the paper formulation and the level of refining. The output of all the properties is made in the unit 40.

In an exemplary embodiment of the present invention, the evaluation of the continuous spectra in accordance with the procedure of the present invention is implemented in a computer, the memory of such computer storing the models and partial models described in detail above. The evaluation in software results in optimum adaptation during the modeling. In particular, linear modeling methods are used for the individual partial models.

At the same time, the modeling can be implemented in a more targeted manner and therefore more accurately than would be achievable with a global model of a measured variable over all material compositions and freenesses. Simultaneously, analytical knowledge can be included. The staged evaluation permits and facilitates the incorporation of analytically known relationships.

Figure 5:
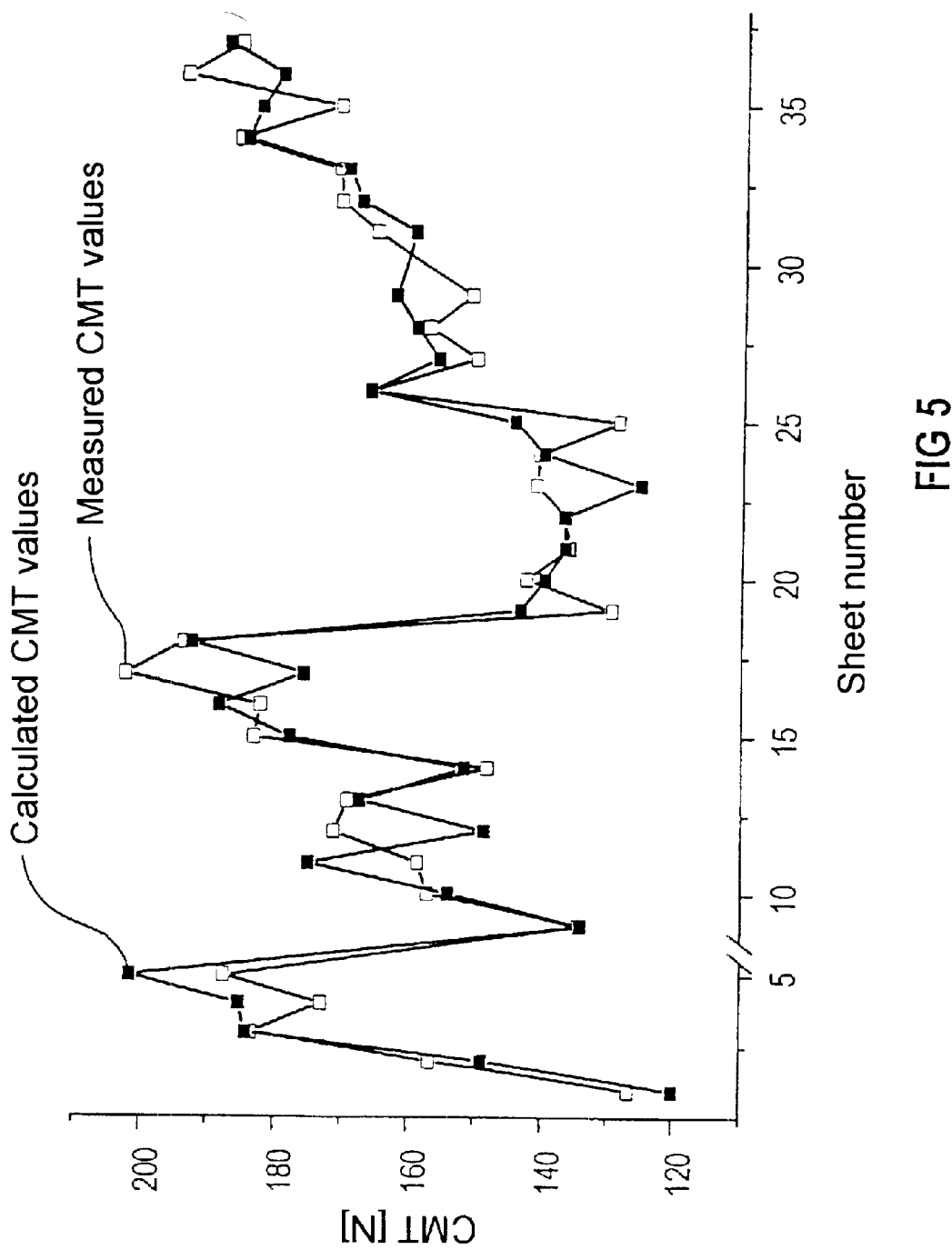
FIG. 5 is a graph illustrating a comparison of calculated and measured CMT values for paper.

The effectiveness of the method of the present invention is illustrated in FIGS. 3 to 7. In particular, for example, the comparisons of measured and calculated values for the freeness SR using FIG. 3 and the light scattering coefficient using FIG. 6 result in unequivocal correlations. The same applies to the representation of the latter variables using FIGS. 4 and 7 for running samples from a collection. In FIG. 5, the CMT value is represented as a characteristic variable which is relevant in practice for the mechanical properties of materials based on chemical pulp, which illustrates a favorable result.

The method of the present invention has been described in detail for paper as the material web. As already indicated, however, this is also correspondingly true of board as a material, or other similar material, containing chemical pulp and mechanical pulp.

Although the present invention has been described in detail with reference to specific exemplary embodiments thereof, various modifications, alterations and adaptations may be made by those skilled in the art without departing from the spirit and scope of the invention. It is intended that the invention be limited only by the appended claims.

What is claimed is:

1. A method of measuring the quality properties of paper and/or board on moving webs, comprising using a contactless optical method to provide continuous optical spectra which are measured and evaluated by chemometric methods comprising a first modeling stage in which basic properties including material composition of the paper or board are determined from the measured spectra; a second modeling stage in which filter properties including freeness of the paper or board are determined from the measured spectra and the basic properties determined in the first stage; and a third modeling stage in which individual variables of said paper or board are determined.

2. The method as claimed in claim 1, wherein said determination of said basic properties of said paper or board comprise determination of grammage of said paper or board.

3. The method as claimed in claim 1, wherein said determination of said basic properties of said paper or board comprise determination of moisture of said paper or board.

4. The method as claimed in claim 1, wherein said determination of said basic properties of the paper or board comprise determination of a thickness of said paper of board.

5. The method as claimed in claim 1, wherein during said determining of said material composition a content of fibrous materials is determined.

6. The method as claimed in claim 1, wherein during said determining of said material composition a content of cellulose material is determined.

7. The method as claimed in claim 1, wherein during said determining of said material composition a content of auxiliary materials is determined.

8. The method as claimed in claim 1, wherein during said determining of said freeness mechanical values of said paper or board are determined.

9. The method as claimed in claim 8, wherein said mechanical values determined comprise tearing lengths.

10. The method as claimed in claim 8, wherein said mechanical values determined comprise bursting strength.

11. The method as claimed in claim 8, wherein said mechanical values determined comprise tear propagation resistance.

12. The method as claimed in claim 8, wherein said mechanical values determined comprise modulus of elasticity.

13. The method as claimed in claim 8, wherein said mechanical values determined comprise extension at break.

14. The method as claimed in claim 1, wherein said determining said individual variables comprises determining optical properties.

15. The method as claimed in claim 14, wherein said optical properties determined comprise a light scattering coefficient.

16. The method as claimed in claim 14, wherein said optical properties determined comprise a light absorption coefficient.

17. The method as claimed in claim 14, wherein said optical properties determined comprise opacity.

18. The method as claimed in claim 14, wherein said optical properties determined comprise a reflectance.

19. The method as claimed in claim 1, further comprising detecting a cross-machine profile of the basic and further properties of the paper or board on the moving web.

20. The method as claimed in claim 19, wherein a measurement of data for determining the input variables for said modeling is carried out on said web without traversing.

21. The method as claimed in claim 20, wherein said measurement is carried out with a sensor array.

* * * * *